US006160137A

United States Patent [19]

Tsuji et al.

[11] Patent Number: 6,160,137

[45] Date of Patent: Dec. 12, 2000

[54] METHOD FOR PRODUCING PROPYLENE OXIDE

[75] Inventors: Junpei Tsuji, Ichihara; Masaru Ishino, Sodegaura; Kenshi Uchida, Yokohama, all of Japan

[73] Assignee: Sumitomo Chemical Company, Limited, Osaka, Japan

[21] Appl. No.: 09/187,088

[22] Filed: Nov. 5, 1998

[30] Foreign Application Priority Data

Nov. 7, 1997 [JP] Japan .................................... 9-305363

[51] Int. Cl.$^{7}$ ...................... C07D 301/19; C07D 301/12; C07D 301/02

[52] U.S. Cl. .......................... 549/523; 549/524; 549/529; 549/531; 549/533

[58] Field of Search .................................... 549/523, 524, 549/529, 531, 533

[56] References Cited

U.S. PATENT DOCUMENTS

| | | | |
|---|---|---|---|
| 3,350,422 | 10/1967 | Kollar | 549/529 |
| 3,634,464 | 1/1972 | Wulff | 549/529 |
| 3,702,855 | 11/1972 | Bell | 549/529 |
| 3,923,843 | 12/1975 | Wulff | 549/529 |
| 4,046,784 | 9/1977 | Gipson | 549/529 |
| 4,521,637 | 6/1985 | Stevens | 568/659 |
| 5,354,875 | 10/1994 | Nemeth | 549/531 |

FOREIGN PATENT DOCUMENTS

| | | |
|---|---|---|
| 50-30049 | 9/1975 | Japan . |
| 54-40525 | 12/1979 | Japan . |
| 54-40526 | 12/1979 | Japan . |
| 56-35941 | 8/1981 | Japan . |
| 8-269031 | 10/1996 | Japan . |

OTHER PUBLICATIONS

Webster's II New Riverside University Dictionary, Defination of Diluent, 1994.

*Primary Examiner*—Alan L. Rotman
*Assistant Examiner*—Rita Desai
*Attorney, Agent, or Firm*—Sughrue, Mion, Zinn, Macpeak & Seas, PLLC

[57] ABSTRACT

A method for producing propylene oxide by reacting a hydroperoxide with propylene by a fixed bed flow reaction in the presence of a titanium-containing solid catalyst, wherein said catalyst is diluted with a diluent comprising a solid inorganic compound which is inactive to the reaction and has a heat conductivity at 400 K of about 10 $Wm^{-1}K^{-1}$ or more.

6 Claims, No Drawings

METHOD FOR PRODUCING PROPYLENE OXIDE

BACKGROUND OF THE INVENTION

1. Field of the Invention

The present invention relates to a method for producing propylene oxide. More particularly, the present invention relates to a method for producing propylene oxide by reacting a hydroperoxide with propylene by a fixed bed flow reaction in the presence of a titanium-containing solid catalyst to improve the selectivity of the intended propylene oxide and to suppress the decomposition of the hydroperoxide.

2. Description of the Related Art

Propylene oxide is one of useful industrial chemicals used for example as a raw material in producing a polyurethane, and the like.

It is known that an olefin-type compound and an organic hydroperoxide are reacted in the presence of a titanium-containing solid catalyst to convert the olefin-type compound into an oxirane compound. The titanium-containing solid catalyst used is usually prepared by a method in which titanium is supported on a silica carrier and the like (see, e.g., Japanese Patent Application Publication (JP-B) Nos. 56-35941, 54-40525, 54-40526 and 50-30049, Japanese Patent Application Laid-Open (JP-A) No. 8-269031, and the like). However, when an epoxidation reaction of propylene is conducted by a fixed bed flow reaction by using a catalyst prepared by these methods, there occurred problems that a unpreferable by-product was formed and the selectivity of propylene oxide was insufficient, and that the decomposition reaction of a hydroperoxide was accelerated due to heat generation.

SUMMARY OF THE INVENTION

Under these circumstances, the present inventors have intensively studied a method for producing propylene oxide which does not have the above-described problems and as a result, found that when propylene oxide is produced by reacting a hydroperoxide with propylene by a fixed bed flow reaction, formation of a by-product can be suppressed, the selectivity of the intended propylene oxide can be improved and the decomposition of the hydroperoxide can be suppressed, by using a titanium-containing solid catalyst diluted with a diluent comprising a solid inorganic compound, and completed the present invention.

Namely, the present invention relates to a method for producing propylene oxide by reacting a hydroperoxide with propylene by a fixed bed flow reaction in the presence of a titanium-containing solid catalyst, wherein said catalyst is diluted with a diluent comprising a solid inorganic compound which is inactive to the reaction and has a heat conductivity at 400 K of about 10 $Wm^{-1}K^{-1}$ or more.

The catalyst used in the present invention is a titanium (hereinafter, described as "Ti")-containing solid catalyst. As the Ti-containing solid catalyst, for example, compounds prepared by supporting a titanium compound on various carriers, compounds complexed with other oxides by a coprecipitation method or sol-gel method, and zeolite-based oxides containing titanium are listed. So-called titanium-silica catalyst containing titanium bonded chemically with solid silica and/or inorganic silicate can be preferably used. This catalyst can be produced by methods disclosed in JP-B Nos. 56-35941, 54-40525, 54-40526, 50-30049 and the like.

An epoxidation reaction is carried out by reacting a hydroperoxide with an olefin by a fixed bed flow reaction by using a Ti-containing solid catalyst.

Examples of the hydroperoxide include organic hydroperoxides.

The organic hydroperoxide is a compound represented by the general formula R—O—O—H (wherein, R is a monovalent hydrocarbyl group), and this reacts with an olefin-type compound to form an oxirane compound and a compound represented by the formula R—OH. Preferably, the group R is a group having 3 to 20 carbon atoms. Most preferably, it is a hydrocarbyl group having 3 to 10 carbon atoms, and particularly a secondary or tertiary alkyl group or aralkyl group. Among them, a tertiary alkyl group and a secondary or tertiary aralkyl group are particularly preferable, and specific examples thereof include a tertiary butyl group, tertiary pentyl group, cyclopentyl group, 1-phenylethyl-1 group and 2-phenylpropyl-2 group, furthermore, there are also listed various tetralinyl groups generated by removing a hydrogen atom from an aliphatic side chain of a tetralin molecule.

When ethylbenzene hydroperoxide is used, the resulting hydroxyl compound is 1-phenylethanol, and it can be converted to styrene by a dehydration reaction. When cumene hydroperoxide is used, the resulting hydroxyl compound is 2-phenyl-2-propanol. This can be converted to α-methylstyrene by a dehydration reaction. Both styrene and α-methylstyrene are industrially useful substances.

Tertiary amylene generated by the dehydration reaction of tertiary pentyl alcohol obtained by using tertiary pentyl hydroperoxide is a useful substance as the precursor of isoprene. Tertiary pentyl alcohol is also useful as the precursor of methyl tertiary pentyl ether which is an octane booster. t-Butyl alcohol obtained by using t-butyl hydroperoxide is a useful substance as the precursor of methyl-t-butyl ether which is an octane booster.

As an example of the hydroperoxide other than organic hydroperoxides, hydrogen peroxide can be listed.

Hydrogen peroxide is a compound represented by the chemical formula HOOH, and can be obtained usually in the form of an aqueous solution. It reacts with an olefin-type compound to form an oxirane compound and water.

The hydroperoxide which is used as a raw material may be a thin or dense purified or non-purified substance.

The epoxidation reaction may also be carried out in a liquid phase by using a solvent. This solvent is preferably a substance which is liquid under the pressure and temperature in the reaction and substantially inactive against the reactants and product. The solvent may be a substance existing in the hydroperoxide solution. For example, when ethylbenzene hydroperoxide (EBHP) is a mixture composed of EBHP and ethylbenzene which is a raw material thereof, ethylbenzene can also be used as a substitute for the solvent without specifically adding the solvent.

As the industrial practical embodiment of the present invention, there is suitably adopted a continuous method by a fixed bed flow reaction which is excellent in economy and operation property.

In the fixed bed flow reaction, for example, a catalyst composed of a solid pellet is kept in a reaction tube, and a hydroperoxide raw solution and propylene may advantageously be allowed to flow through the tube. The reaction temperature is preferably from about 0° C. to about 200 C, and more preferably from about 30° C. to about 150° C. When the temperature is lower, the reaction speed may sometimes become slow, and when the temperature is higher, the reaction selectivity may sometimes decrease. The reaction pressure is preferably from about 1 atm to about 100 atm, and more preferably from about 10 atm to about 70 atm. When the pressure is lower, propylene may vaporize, and on the contrary, when the pressure is higher, equipment cost may become too high.

The characteristic of the method of the present invention is in the use of a solid inorganic compound which is inactive against the reaction and has a heat conductivity at 400 K of about 10 $Wm^{-1}K^{-1}$ or more, preferably about 20 $Wm^{-1}K^{-1}$ or more as a diluent for the catalyst to be filled in a fixed bed flow reaction vessel. The heat conductivity of a solid inorganic compound can be measured in general by using a stationary heat flow method (for example, a method in which a heat source is placed on one end of a cylindrical sample, and temperatures are measured at two points having different distances from the heat source at stationary condition). The details of the measuring method are described in a book "$4^{th}$ edition Shin Jikken Kagaku Koza" (published by MARUZEN Co.), vol. 4, p. 419, and the values of the heat conductivity of various solid inorganic compounds are described in a book "Kagaku Binran" (Nippon Kagaku Kai edit., published by MARUZEN Co.) and the like. By diluting a catalyst using as a diluent an inorganic compound having a heat conductivity at 400 K of about 10 $Wm^{-1}K^{-1}$ or more measured by as described above and by conducting the reaction, the formation of a by-product can be suppressed, and the selectivity of the intended propylene oxide (hereinafter, described as "PO") can be enhanced. Furthermore, the decomposition reaction of hydroperoxide can be suppressed (the reason for this is hypothesized that local and steep increase in temperature in a catalyst bed due to epoxidation reaction heat is suppressed by use of a diluent).

Examples of the solid inorganic compound include metal oxides, metal carbides, metal nitrides, as well as other various solid ceramics. It is preferable that the solid inorganic compound has small surface area since the diluent is required to be in active against the reaction. Therefore, the surface area of the diluent is preferably about 100 $m^2/g$ or less, more preferably about 10 $m^2/g$ or less, further preferably about 1 $m^2/g$ or less. Specific examples of such diluents include alumina, magnesia, silicon carbide and the like, and the use of α-alumina having low surface area is particularly preferable.

As the method for diluting a catalyst with such a diluent, there are listed a method in which a diluent is filled in a reaction vessel together with a catalyst formed, a method in which a formed mixture of a catalyst and a diluent is filled in a reaction vessel, and the like, however, the dilution method is not limited to them.

The addition ratio (dilution ratio) of a diluent to a catalyst is not particularly restricted, and preferably from about 10% by weight to about 90% by weight, more preferably from about 30% by weight to about 70% by weight When the dilution ratio is too low, the effect for improving the PO selectivity may sometimes be poor, and when the dilution ratio is too high, sometimes the reaction vessel volume may increase, the productivity may decrease and economical efficiency may lower.

Unreacted propylene in thus obtained epoxidation reaction solution can be recycled to the epoxidation reaction process again after separation by distillation. The separation of propylene oxide from the reaction solution after most of the unreacted propylene has been removed can be easily conducted by usual operation such as distillation, washing and the like.

According to the present invention, when propylene oxide is produced by reacting hydroperoxide with propylene by a fixed bed flow reaction in the presence of a titanium-containing solid catalyst, formation of a by-product can be suppressed, the selectivity of the intended propylene oxide can be enhanced and the decomposition of the hydroperoxide can be suppressed.

EXAMPLE

Reference Example 1

A commercially available silica gel (10 to 40 mesh, surface area 300 $m^2$, average pore size 10 nm, 50 g), tetraisopropyl titanate (2.2 g), acetylacetone (1.64 g) and isopropanol (200 ml) were mixed, stirred for 30 minutes at room temperature, then, the mixture was filtered. The solid part was immersed in isopropanol (50 ml), stirred, washed, then, the solution was separated by filtration. This procedure was repeated three times. The solid part was dried at 500° C. for 2 hours under nitrogen flow. It was further calcinated for 4 hours at 600° C. under air flow. This substance (10 g), hexamethyldisilazane (4 g) and toluene (50 g) were mixed, and stirred with heating for 1 hour at 200° C. under pressure. The liquid part was distilled off from the mixture by filtration. It was washed with toluene (50 g), and dried under reduced pressure (120° C., 10 mmHg, 3 hours) to obtain a catalyst.

[Alkali washing of EBHP solution]

An EBHP solution (15% by weight, 3000 g) and sodium hydroxide (0.5 g by weight, 1000 g) were stirred with mixing for 15 minutes at 60° C., allowed to stand still for 15 minutes at the same temperature, then, the solution was separated. The separated oil layer was washed with 1000 g of water at 60° C. for 15 minutes. The resulted oil layer was concentrated at 60° C., 50 mmHg, to obtain a 35 wt % EBHP solution.

Example 1

A catalyst synthesized according to the preparation method of Reference Example 1 (Ti content: 0.7% by weight) was diluted with α-alumina (heat conductivity at 400 K: 26 $Wm^{-1}K^{-1}$) at a volume ratio of 1:1 and the mixture was filled in a reaction vessel, and an epoxidation reaction was conducted in a fixed bed flow reaction apparatus using an EBHP solution (EBHP 35% by weight, EB 58% by weight) obtained by the washing method of Reference Example 1 and propylene. A stainless steal tube having an internal diameter of 10 mm was used as a reaction tube, and a thermocouple was inserted into the tube and inner temperature was measured. The reaction was conducted at a propylene/EBHP molar ratio=12, a LHSV=6 $h^{-1}$ in terms of the total flow amount of the EBHP solution and propylene to catalyst volume containing no diluent, and a reaction pressure of 40 $kg/cm^2$. The results are shown in Table 1.

Comparative Example 1

The reaction was conducted in the same manner as in Example 1 except that the catalyst was diluted with silica (heat conductivity at 400 K: 1 $Wm^{-1}K^{-1}$) at a volume ratio of 1:1. The results are shown in Table 1.

Comparative Example 2

The reaction was conducted in the same manner as in Example 1 except that the dilution of the catalyst was not conducted. The results are shown in Table 1.

In Example 1 satisfying the conditions of the present invention, the reaction temperature decreases, the temperature increase in a catalyst bed is small, and the selectivity of the intended propylene oxide becomes high. Formation of acetophenone which is a decomposition product of ethylbenzene hydroperoxide is low. On the other hand, in Comparative Example 1 in which a diluent having low heat conductivity at 400 K is used and Comparative Example 2 in which a diluent is not used, formation of acetophenone which is a by-product is large, and the selectivity of the intended propylene oxide is low.

TABLE 1

| | Example 1 | Comparative example 1 | Comparative example 2 |
|---|---|---|---|
| Reaction temperature °C. | | | |
| Inlet temperature of catalyst bed | 57.2 | 70.3 | 72.6 |
| Maximum temperature of catalyst bed | 59.7 | 78.5 | 79.4 |
| ΔT | 2.5 | 8.2 | 6.8 |
| Reaction result | | | |
| EBHP conversion | 86.9 | 90.0 | 90.5 |
| PO selectivity | 97.5 | 91.3 | 93.9 |
| ACP selectivity | 1.1 | 2.0 | 2.2 |

ΔT: Temperature increase in catalyst bed (° C.)
ACP: Acetophenone (decomposition product of EBHP)

$$\text{PO selectivity} = \frac{\text{PO produced (mol)}}{\text{EBHP reacted (mol)}} \times 100(\%)$$

$$\text{ACP selectivity} = \frac{\text{ACP produced (mol)}}{\text{EBHP reacted (mol)}} \times 100(\%)$$

What is claimed is:

1. A method for producing propylene oxide, comprising the step of reacting a hydroperoxide with propylene by a fixed bed flow reaction in the presence of a titanium-containing solid catalyst, wherein said catalyst is diluted with a diluent comprising a alumina which is inactive to the reaction and has a heat conductivity at 400 K of about 10 $Wm^{-1}K^{-1}$ or more.

2. The method according to claim 1, wherein the hydroperoxide is an organic hydroperoxide.

3. The method according to claim 2, wherein the organic hydroperoxide is ethylbenzene hydroperoxide.

4. The method according to claim 1, wherein the diluent is a diluent comprising a solid inorganic compound which has a heat conductivity at 400 K of about 20 $Wm^{-1}K^{-1}$ or more.

5. The method according to claim 1, wherein the diluent is a diluent having a surface area of about 10 $m^2/g$ or less.

6. The method according to claim 1, wherein the diluent is a diluent having a surface area of about 1 $m^2/g$ or less.

* * * * *